United States Patent [19]

Yamada et al.

[11] Patent Number: 5,340,931
[45] Date of Patent: Aug. 23, 1994

[54] AROMATIC ALLENE COMPOUNDS OF THE FORMULA $(CH_2=CH-O)_n-R-(A)_m$ IN WHICH R IS AN AROMATIC GROUP AND PREPARATION THEREOF

[75] Inventors: Mitsuo Yamada; Hiromichi Kayano, both of Osaka; Kei Aoki, Nara; Keizou Ishii, Hyogo, all of Japan

[73] Assignee: Nippon Paint Co., Ltd., Osaka, Japan

[21] Appl. No.: 323,786

[22] Filed: Mar. 15, 1989

[30] Foreign Application Priority Data

| Mar. 15, 1988 | [JP] | Japan | 63-61119 |
| Mar. 15, 1988 | [JP] | Japan | 63-61120 |
| Mar. 15, 1988 | [JP] | Japan | 63-61121 |
| Mar. 15, 1988 | [JP] | Japan | 63-61122 |
| Mar. 15, 1988 | [JP] | Japan | 63-61123 |

[51] Int. Cl.$^5$ .................. C07C 43/215; C07C 41/18; C07C 41/32
[52] U.S. Cl. .................. 534/843; 534/596; 534/845; 534/851; 562/76; 562/466; 562/467; 562/468; 562/469; 562/473; 568/631; 568/632
[58] Field of Search .............. 534/859, 596, 843, 845, 534/851; 568/657, 654, 687, 688, 631, 632, 633, 634, 640, 641, 642, 643, 649; 562/76, 466, 467, 468, 469, 473

[56] References Cited

U.S. PATENT DOCUMENTS

| 4,885,403 | 12/1989 | Inbasekaran et al. | 568/631 |
| 4,916,203 | 4/1990 | Pigneri et al. | 525/481 X |
| 4,946,865 | 8/1990 | Takahashi et al. | 568/631 X |

OTHER PUBLICATIONS

Mitsunobu, O., "The Use of Diethyl Azodicarboxylate and Triphenylphosphine in Synthesis and Transformation of Natural Products", Synthesis, 1981, 1-28.
Fieser and Fieser, "Reagents for Organic Synthesis", vol. 1 (1967), 1307; vol. 4 (1974), 583; vol. 7, (1979), 432; vol. 10 (1982), 467.
Filippova et al., Chemical Abstracts, vol. 88, No. 190287m (1978).
Filippova et al., Chemical Abstracts, vol. 107, No. 39300a (1987).
Sarcevic et al., Helv. Chim. Acta, 56(5), 1457-76(1973).
Borresen et al., J. Org. Chem., 41(4), 1976, pp. 678-681.
Hatch et al., J. Amer. Chem. Soc., vol. 77, pp. 1798 to 1800 (1955).
Hurd et al., J. Amer. Chem. Soc., vol. 53, pp. 1068 to 1069 (1931).
Fieser et al., "Reagents for Organic Synthesis", vol. UME 2, pp. 336-337 (1969).
Theelheimer, "Synthetic Methods of Organic Chemistry," vol. 20, p. 439 #538 (1966).

*Primary Examiner*—Robert W. Ramsuer
*Assistant Examiner*—Fiona T. Powers
*Attorney, Agent, or Firm*—Wendroth, Lind & Ponack

[57] ABSTRACT

Allene compounds have the formula:

$$(CH_2=C=CH-O)_n-R-(A)_m \qquad (I)$$

in which R is a substituted or unsubstituted mono- or polyvalent benzene, naphthalene, anthracene, azobenzene, bisphenol or polyphenyl (containing 2 to 10 benzene rings connected in line) nucleus, or a group $$-Ph-R^1-Ph- \qquad (II)$$

(in which each group Ph is a phenylene, halophenylene, alkylphenylene, cyanophenylene or alkoxyphenylene group, and the chain $R^1$ linking the two group Ph is a $C_1$-$C_6$ aliphatic hydrocarbon or an alicyclic hydrocarbon group, the chain optionally being interrupted by one or more oxygen atoms); A is a carboxyl or sulphonyl group or a group $-CH=C=CH_2$; n is an integer of from 1 to 10; m is 0, 1, 2 or 3; and the sum of m and n is equal to the valence of the group R.

They may be prepared by isomerization of corresponding propargyloxy compounds.

6 Claims, No Drawings

AROMATIC ALLENE COMPOUNDS OF THE FORMULA $(CH_2=CH-O)_n-R-(A)_m$ IN WHICH R IS AN AROMATIC GROUP AND PREPARATION THEREOF

FIELD OF THE INVENTION

The present invention relates to novel aromatic allene compounds and preparation thereof.

BACKGROUND OF THE INVENTION

Public attention has been directed to phenoxyallene compounds and their polymerized products since a radical polymerization of phenoxyallene compound of the formula:

$$CH_2=C=CH-O-C_6H_5$$

was first reported in Polymer Preprints, Japan 35(2),133 (1986).

The publication also indicates certain substituted phenoxy allene compounds as cyano- or methoxy-substitued phenoxy allene compounds.

Such a compound has in its molecule an allenyl group in which 3 carbon atoms are connected in line with two separate double bonds, and therefore, it is radically polymerizable just as a vinyl monomer. Moreover, thus formed polymer includes, in its main chain, the following repeating units:

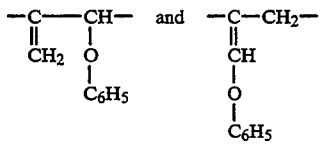

and said vinyl ether group and allyl group are ionically or radically polymerizable with other vinyl monomers and said phenoxy group is still reactive with other materials.

Therefore, this polymer can be used as a starting material for the synthesis of other novel polymeric substances which are expected to be useful as resinous vehicle in paint and for other uses in various technical fields.

Nevertheless, the known aromatic allene compounds are quite limited in number.

An object of this invention is, therefore, to provide a novel class of aromatic allene compounds. An additional object is to provide an industrially and economically acceptable method for the preparation of such allene compounds.

SUMMARY OF THE INVENTION

According to the invention, are provided novel aromatic allene compounds represented by the formula:

$$(CH_2=C=CH-O-)_n-R-(A)_m \quad (I)$$

wherein R represents a substituted or unsubstituted mono- or poly-valent benzene, naphthalene, anthracene, azobenzene, bisphenol or polyphenyl (containing 2 to 10 benzene rings connected in line) nucleus, or a group $$-Ph-R^1-Ph- \quad (II)$$

in which each group Ph is a phenylene, halophenylene, alkylphenylene, cyanophenylene or alkoxyphenylene group, and the chain $R^1$ linking the two groups Ph is a $C_1$-$C_6$ aliphatic hydrocarbyl or an alicyclic hydrocarbyl group, the chain optionally being interrupted by one or more oxygen atoms); A is a carboxyl (—COOH) or sulphonyl (—SO$_3$H) group or a group —CH=C=CH$_2$; n is an integer of from 1 to 10; m is 0, 1, 2 or 3 and the sum of m and n is equal to the valence of the group R, except to exclude the cases in which R is benzene, cyanobenzene or methoxybenzene and n is 1, m is 0.

More specifically, the invention provides the following novel aromatic allene compounds.

(A) Polycyclic phenoxyallene compounds of the formula:

$$(CH_2=C=CH-O-)_n R$$

wherein R is a polycyclic aromatic hydrocarbon residue selected from the group consisting of naphthalene, anthracene, polyphenyl having 2 to 10 benzene rings connected in line each other, azobenzene and their nuclear substituted derivatives; and n is an integer of 1 to 3. This class of polycyclic phenoxyallene compounds may be advantageously prepared by the method wherein a polycyclic phenol compound of the formula: $(HO-)_n R$ (in which R and n are as defined above) is reacted with a propargyl halide to obtain a propargyloxy polycyclic phenyl compound, which is then subjected to an allenylization under basic conditions.

As the starting materials, the following are advantageously used:

Polycyclic phenol compounds as, for example, α-naphthol, β-naphthol, 2,6-dihydroxynaphthalene, naphthoresorcin, 2-oxy-anthracene, 9-Oxyanthracene, 1,2-dioxyanthracene, 1,8-dioxyanthracene, 2,3-dioxyanthracene, 2,6-dioxyanthracene, 2,7dioxyanthracene, 1,9-dioxyanthracene, 9,10-dioxyanthracene, o-phenylphenol, m-phenylphenol, p-phenylphenol, 4,4'-biphenol, 2,2'-biphenol, p-hydroxyazobenzene, dioxy derivatives of polyphenyl having 2 to 10 benzene rings connected in line each other and their halogen, alkyl, cyano, alkoxy or acyl derivatives; and propargyl halides as propargyl bromide and the like.

The first step reaction may be advantageously carried out in the presence of alkali and the second isomerization reaction under basic conditions, as, for example, in the presence of potassium alcoholate of t-butanol.

(B) Phenoxy allene compounds bearing polar groups:

$$(CH_2=C=CH-O-)_n R-(A)_m$$

wherein R is an aromatic hydrocarbon residue selected from the group consisting of benzene, naphthalene, anthracene, azobenzene, bisphenol, polyphenyl having 2 to 10 benzene rings connected in line each other, and their halogen, alkyl, cyano or alkoxy substituted derivatives; A is —COOH or —SO$_3$H; n is an integer of 1 to 10 and m is an integer of 1 to 3.

This class of allene compounds may be advantageously prepared as in group (A) compounds, but using the phenols of the formula:

$$(HO-)_n-R-(A)_m$$

as the starting materials.

Examples of such phenols are o-hydroxy benzoic acid, m-hydroxybenzoic acid, p-hydroxy benzoic acid, p-hydroxy benzene sulfonic acid, o-cresol sulfonic acid, p-hydroxy benzene acetic acid, p-hydroxy benzene propionic acid, 1-naphthol-2-carboxylic acid, 2-naphthol-3-carboxylic acid, 2-naphthol-6-carboxylic acid, 1-naphthol-4-sulfonic acid, 1-naphthol-8-sulfonic acid, 2-naphthol-6-sulfonic acid, 1,4-dihydroxy-2-naphthoic acid, 1-naphthol-3,6-disulfonic acid, 4'-hydroxybiphenyl-4-carboxylic acid, 2,2'-biphenol-3-carboxylic acid, 4-hydroxybiphenyl-3-carboxylic acid, 2-hydroxybiphenyl-3-carboxylic acid, 2-(4'hydroxybenzeneazo)-benzoic acid, 2,2'-bis(4-hydroxyphenyl)-1carboxylpropane and the like.

(C) Polyfunctional phenoxy allene compounds:

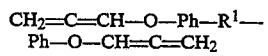

wherein Ph stands for phenyl group, halogenated phenyl group, alkyl substituted phenyl group, cyano substituted phenyl group or alkoxy substituted phenyl group; $R^1$ is a member selected from aliphatic hydrocarbons having 1 to 6 carbon atoms, alicyclic hydrocarbons, aliphatic or alicyclic hydrocarbons containing one or more ether bonds. This class of phenoxy allene compounds may also be prepared as in the group (A) compounds, using a polyphenol compound the formula:

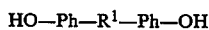

and a propargyl halide as starting materials.

Examples of such polyphenol compounds are bis(2-hydroxyphenyl)methane, bis(3-hydroxyphenyl)methane, bis(4-hydroxyphenyl)methane, bis(2-hydroxy-4-methylphenyl) methane, bis(2-hydroxy-5-methylphenyl)methane, bis(2-hydroxy-6-methylphenyl)methane, bis(4-hydroxy-2-methylphenyl)methane, bis(4-hydroxy-3-methylphenyl)methane, bis(3-hydroxy-2,4,6-trimethylphenyl)methane, bis(2-hydroxy-4-propylphenyl)methane, bis(4-hydroxy-2-propylphenyl)methane, bis(4-hydroxy-2 -methyl-6-ethylphenyl)methane, bis(4-hydroxy-2,3,5,6-tetramethylphenyl)methane, bis(2-hydroxy-4-tert-butylphenyl)methane, bis(4-hydroxy-2-methyl-5-isopropylphenyl)methane, bis(4-hydroxy-3-methyl-6-isopropylphenyl)methane, bis(4-hydroxy-2-tert-butyl-5-methylphenyl)methane, bis(4-hydroxy-2,6-di-tert-butylphenyl)methane, bis(4-hydroxy-2-chlorophenyl)methane, bis(4-hydroxy-2,6-dichlorophenyl)methane, bis(2-hydroxy-4-bromophenyl)methane, bis(3-hydroxy-2,4,6-trichlorophenyl)methane, bis(4-hydroxy-2-methoxyphenyl)methane, 2,2-bis(4-hydroxyphenyl)propane, 2,2-bis(4-hydroxy-2-methylphenyl)propane, 2,2-bis(4-hydroxy-2,6-dibromophenyl)propane, 1,1-bis(4-hydroxyphenyl)-cyclohexane and the like.

(D) Polyvalent allene compounds of the formula:

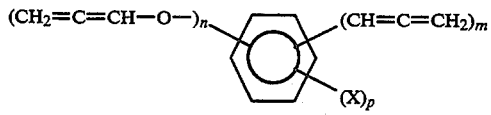

wherein X is hydrogen atom, halogen atom, alkyl group, cyano group or alkoxy group; n is an integer of 1 to 4; m is 0 or 1 or 2; p is 0 or an integer of 1 to 4, providing $m+n \geq 2$, and $m+n+p=6$.

This class of allene compounds may be advantageously prepared by either one of the following methods:

(1) The first method comprises the combination of steps of reacting one mole of a phenol compound of the formula:

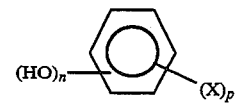

in which X is a hydrogen atom, a halogen atom, an alkyl group, a cyano group or an alkoxy group; n is an integer of 1 to 4; and p is 0 or an integer of 1 to 4, providing that the sum of n and p is 6, with n+m moles (in which m is 0 or 1 or 2; n is an integer of 1 to 4, providing $m+n \geq 2$) of propargyl halide to give a phenyl propargyl ether of the formula:

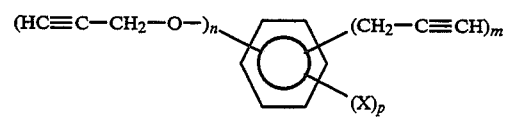

(in which X,n,p and m are as defined above, providing $m+n \geq 2$, and $m+n+p=6$) and subjecting thus obtained phenylpropargylether to an allenylization under basic conditions.

(2) The second method comprises reacting one mole of phenylpropargylether of the formula:

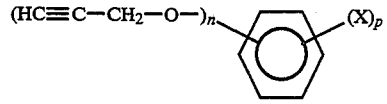

(in which X is hydrogen atom, halogen atom, alkyl group, cyano or alkoxy; n is an integer of 1 to 4, p is 0 or an integer of 1 to 4, providing the sum of n and p is 6) with m moles (m=1 or 2) of propargyl halide through a Friedel Crafts reaction, to give a polyvalent propargyl compound of the formula:

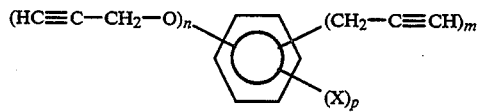

(in which X,n and p are as defined above, m is 1 or 2 and $m+n+p=6$) and subjecting thus obtained propargyl compound to an allenylization under basic conditions.

When a large excess amount of halogenated propargyl are reacted with a phenol compound, there is a possibility of forming certain amounts of by-products in which only a part of the hydroxyl groups are changed to propargylethers and where there still remains an amount of unchanged hydroxyl groups. However, such by-products may be easily separated out by using a thin layer chromatography and the like.

A Friedel Crafts reaction of said phenoxypropargylether with a propargyl halide may be easily carried out in an inert solvent in the presence of a Lewis acid catalyst as an anhydrous aluminium chloride and one or two propargylo groups may be effectively introduced in the phenyl nucleus. The allenylization of propargyl group may be easily carried out by using potassium alcoholate of t-butanol under basic conditions.

These allene compounds are all novel and are very useful as the reactive monomers for the preparation of vinyl resins, since they can be homopolymerized or copolymerized with other known $\alpha,\beta$-ethylenically unsaturated compounds.

As already mentioned, they can easily be obtained by a generic method comprising reacting a phenol with a propargyl halide and converting thus obtained phenylpropargylether to an allene compound through an isomerization in the presence of potassium alcoholate of t-butanol under basic conditions. However, the same compounds can also be synthesized more economically without using an expensive propargyl halide. That is, in a more advantageous method, a propargyl alcohol is directly reacted with a phenol or an alkali metal phenolate of the formula:

R—OX in which R is a substituted or unsubstituted aromatic hydrocarbon residue; and X is hydrogen or alkali metal, in the presence of a dehydration agent selected from dicyclohexylcarbodiimide-cupric chloride, azodicarboxylic acid ester-triphenylphosphine, triphenylphosphine-carbon tetrachloride and hexamethylphosphorous triamide phosphonium base, to give a propargylarylether of the formula:

R—O—CH$_2$—C≡CH and the thus obtained propargylarylether is subsequently subjected to allenylization under basic conditions. Among the abovementioned dehydration agents, dicyclohexylcarbodiimide-cupric chloride system is particularly useful for the reaction of phenol and propargyl alcohol, and other members are for the reaction of alkali metal phenolate and propargyl alcohol.

In the actual reaction, the abovementioned phenol, propargyl alcohol, and dehydration agent are placed in an appropriate inert solvent as, for example, tetrahydrofuran, benzene, toluene, xylene, ester or the like, and reacted at a room temperature to 120° C., preferably 50° to 100° C. This reaction may be smoothly proceeded to give the arylpropargylether, which is then treated, for example, with potassium alcoholate of t-butanol to give the desired allene compound in a very higher reaction yield.

The invention shall be now more fully explained in the following examples. Unless otherwise being stated, all parts and % are by weight.

EXAMPLE 1

Into a reaction flask fitted with a stirrer, a thermometer, a nitrogen gas inlet tube and a reflux condenser, was placed 21.259 parts of 1-naphthol, 53.086 parts of deionized water, 6.675 parts of NaOH and 0.120 part of tetrabutylammoniumbromide and to this mixture, 18.859 parts of propargyl bromide was added dropwise and reacted at 80° C. for 6 hours. After completion of the reaction, the content was treated with a mixture of ether and deionized water and the ether layer was separated, added with magnesium sulfate and kept stand overnight. After filtering off magnesium sulfate, the ether solvent was removed by an evaporator and the residue was subjected to a column chromatography (silica gel 200 mesh) to obtain a purified 1propargyloxynaphthalene. Yield 63.6%

Into a similar reaction vessel as used in the abovementioned reaction, were placed 1.532 parts of t-BuOK and 6.816 parts of t-BuOH and to this, a mixture of 10.000 parts of 1-propargyloxynaphthalene and 23.333 parts of t-BuOH was dropwise added. The content was reacted at 50° C. for 60 minutes and then deionized water was added to stop the reaction. t-BuOH layer and water layer were removed off by using an evaporator, and the residue was added with an aqueous NaOH solution, extracted with an ether and the ether layer was separated. The ether solvent was removed off and the residue was subjected to a column chromatography (silica gel 200 mesh) to obtain a purified 1-allenyloxy naphthalene as a colorless oily product.

This compound was identified by FT-NMR(H) and IR spectrum. The reaction yield was 43.0%.

| | CH$_2$=C=CH—O—C$_{10}$H$_7$ | |
|---|---|---|
| IR | | (cm$^{-1}$) |
| (CH$_2$=C=CH—) | | 1970–1950 |
| $\nu$(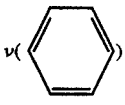) | | 1630–1580 |
| $\nu$(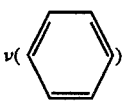) | | 1530–1480 |
| $\nu$(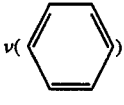) | | 1420–1380 |
| $\nu$(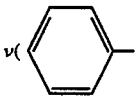—O—CH=) | | 1260–1200 |
| $^1$H-NMR | | (test solvent: CDCl$_3$) |
| | | (standard: tetramethyl silan) |
| | | $\delta$(ppm) |
| CH$_2$=C=C— (2H, d) | | 5.42–5.45 |
| =C=CH—O— (1H, t) | | 6.89–6.98 |
| Ph—H (7H, m) | | 7.20–8.00 |

EXAMPLE 2

Into a reaction flask fitted with a stirrer, a thermometer, a nitrogen gas inlet tube and a reflux condenser, were placed 26.677 parts of 2-hydroxyanthracene, 49.444 parts of deionized water, 6.217 parts of NaOH and 0.096 part of tetrabutylammonium bromide and to this mixture, 18.859 parts of propargyl bromide was added dropwise and reacted at 80° C. for 6 hours. After completion of the reaction, the content was treated with a mixture of ethyl acetate and deionized water and the ethyl acetate layer was separated, added with magnesium sulfate and kept standing overnight to effect dehydration. After filtering off magnesium sulfate, the solvent was removed off by an evaporator and the residue was subjected to a column chromatography (silica gel 200 mesh) to obtain a purified 2propargyloxyanthracene. Yield 43.6%

Into a similar reaction vessel, as used in the above-mentioned reaction, were placed 1.203 parts of t-BuOK and 6.816 parts of THF and to this, a mixture of 10.000 parts of 2-propargyloxyanthracene and 23.333 parts of THF was added dropwise. The content was reacted at 50° C. for 60 minutes and then a deionized water was added to stop the reaction. THF layer and water layer were removed off by using an evaporator, and the residue was subjected to a column chromatography (silica gel 200 mesh) to obtain a purified 2-allenyloxy anthracene as colorless crystals (M.P. 90.3°–95.6° C).

This compound was identified by FT-NMR(H) and IR spectrum. The reaction yield was 56.5%.

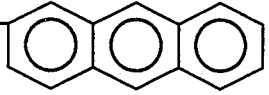

| IR | (cm$^{-1}$) |
|---|---|
| $\nu$(CH$_2$=C=CH—) | 1970–1950 |
|  | 1630–1580 |
|  | 1520–1485 |
|  | 1260–1200 |

| $^1$H-NMR | (test solvent: CDCl$_3$) (standard: tetramethyl silan) $\delta$(ppm) |
|---|---|
| CH$_2$=C=C— (2H, t) | 5.44–5.45 |
| =C=CH—O— (1H, t) | 6.89–6.98 |
| Ph—H (9H, m) | 7.10–7.83 |

EXAMPLE 3

Into a reaction flask fitted with a stirrer, a thermometer, a nitrogen gas inlet tube and a reflux condenser, were placed 24.140 parts of p-hydroxybiphenyl, 51.120 parts of deionized water, 6.427 parts of NaOH and 0.127 part of tetrabutylammonium bromide and to this mixture, 18.161 parts of propargyl bromide was added dropwise and reacted at 80° C. for 6 hours. After completion of the reaction, the content was treated with an aqueous NaOH solution and then subjected to a fractionation with ethyl acetate. Thereafter, magnesium sulfate was added and the mixture was kept standing overnight to effect dehydration. After filtering off magnesium sulfate, the solvent was removed off by an evaporator and the residue was subjected to a column chromatography (silica gel 200 mesh) to obtain a purified 1-propargyloxybiphenyl. Yield 53.1%

Into a similar reaction vessel, as used in the above-mentioned reaction, were placed 1.342 parts of t-BuOK and 7.607 parts of THF and to this, a mixture of 10.000 parts of 1propargyloxybiphenyl and 23.333 parts of THF was added dropwise. The content was reacted at 50° C. for 60 minutes and then a deionized water was added to stop the reaction. THF layer and water layer were removed by using an evaporator, and the residue was subjected to a column chromatography (silica gel 200 mesh) to obtain a purified 1-allenyloxy biphenyl as colorless oily product. This compound was identified by FT-NMR(H) and IR spectrum. The reaction yield was 63.2%.

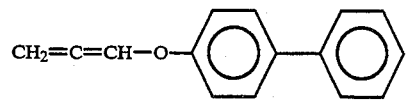

| IR | (cm$^{-1}$) |
|---|---|
| $\nu$(CH$_2$=C=CH—) | 1970–1950 |
|  | 1630–1580 |
|  | 1525–1480 |
|  | 1260–1200 |

| $^1$HMR | (test solvent: CDCl$_3$) (standard: tetramethyl silan) $\delta$(ppm) |
|---|---|
| CH$_2$=C=C— (2H, d) | 5.42–5.52 |
| =C=CH—O— (1H, t) | 6.80–6.99 |
| Ph—H (9H, m) | 7.10–7.61 |

EXAMPLE 4

Into a reaction flask fitted with a stirrer, a thermometer, a nitrogen gas inlet tube and a reflux condenser, were placed 21.028 parts of 2,7-dihydroxynaphthalene, 46.103 parts of deionized water, 11.593 parts of NaOH and 0,112 part of tetrabutylammonium bromide and to this mixture, 32.756 parts of propargyl bromide was added dropwise and reacted at 80° C. for 6 hours. After completion of the reaction, the content was treated with a mixture of ether and diionized water and the ether layer was separated. Thereafter, magnesium sulfate was added and the mixture was kept standing overnight to effect dehydration. After filtering off magnesium sulfate, the solvent was removed off by an evaporator and the residue was subjected to a column chromatography (silica gel 200 mesh) to obtain a purified 2,7-dipropargyloxynaphthalene. Yield 43.6%

Into a similar reaction vessel, as used in the above-mentioned reaction, were placed 2.316 parts of t-BuOK and 13.108 parts of THF and to this, a mixture of 10,000 parts of 2,7-dipropargyloxynaphthalene and 23.333 parts of THF was added dropwise. The content was reacted at 50° C. for 60 minutes and then a deionized water was added to stop the reaction. THF layer and water layer were removed off by using an evaporator, and the residue was subjected to a column chromatography (silica gel 200 mesh) to obtain a purified 2,7-diallenyloxy naphthalene as white rystals (M.P. 80.5°–83.5° C.)

This compound was identified by FT-NMR(H) and IR spectrum. The reaction yield was 45.3%.

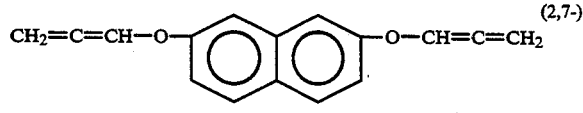

| IR | (cm⁻¹) |
|---|---|
| $\nu$(CH$_2$=C=CH—) | 1970–1950 |
| $\nu$(phenyl) | 1630–1580 |
| $\nu$(phenyl) | 1525–1480 |
| $\nu$(phenyl—O—CH=) | 1260–1200 |

| ¹H-NMR | (test solvent: CDCl$_3$) (standard: tetramethyl silan) $\delta$(ppm) |
|---|---|
| C$\underline{H}_2$=C=C— (4H, d) | 5.39–5.52 |
| =C=C$\underline{H}$—O— (2H, t) | 6.80–7.05 |
| Ph—$\underline{H}$ (6H, m) | 7.15–7.92 |

EXAMPLE 5

Into a reaction flask fitted with a stirrer, a thermometer, a nitrogen gas inlet tube and a reflux condenser, was placed 20.814 parts of 4,4'-biphenol, 40.285 parts of deionized water, 10.131 parts of NaOH and 0.133 part of tetrabutylammonium bromide and to this mixture, 28.623 parts of propargyl bromide was added dropwise and reacted at 80° C. for 6 hours. After completion of the reaction, the content was treated with a mixture of ethyl acetate and deionized water and then ethyl acetate layer was fractionated. Thereafter, magnesium sulfate was added and the mixture was kept standing overnight to effect dehydration. After filtering off magnesium sulfate, the solvent was removed off by an evaporator and the residue was subjected to a column chromatography (silica gel 200 mesh) to obtain a purified 4,4'-dipropargyloxybiphenyl. Yield 42.2%

Into a similar reaction vessel, as used in the above-mentioned reaction, were placed 2.124 parts of t-BuOK and 12.036 parts of THF and to this, a mixture of 10.000 parts of 4,4'-dipropargyloxybiphenyl and 23.333 parts of THF was added dropwise. The content was reacted at 50° C. for 60 minutes and then a deionized water was added to stop the reaction. THF layer and water layer were removed by using an evaporator, and the residue was subjected to a column chromatography (silica gel 200 mesh) to obtain a purified 4,4'-diallenyloxy biphenyl as pale yellow crystals (M.P.135.2°–138.5° C.)

This compound was identified by FT-NMR(H) and IR spectrum. The reaction yield was 35.3%.

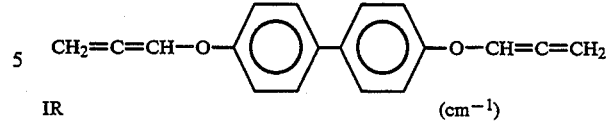

| IR | (cm⁻¹) |
|---|---|
| $\nu$(CH$_2$=C=CH—) | 1970–1950 |
| $\nu$(phenyl) | 1630–1595 |
| $\nu$(phenyl) | 1525–1460 |
| $\nu$(phenyl—O—CH=) | 1260–1200 |

| ¹H-NMR | (test solvent: CDCl$_3$) (standard: tetramethyl silan) $\delta$(ppm) |
|---|---|
| C$\underline{H}_2$=C=C— (4H, d) | 5.42–5.55 |
| =C=C$\underline{H}$—O— (2H, t) | 6.89–6.99 |
| Ph—$\underline{H}$ (8H, m) | 7.00–7.71 |

EXAMPLES 6 TO 9

The same experiments as stated in Example 1 were repeated using various hydroxy compounds and the following allene compounds were obtained.

[Example 6]
4,4'-diallenyloxy-3-chlorobiphenyl
yield 54.0%
as pale yellow crystals M.P. 140.5°–143.3° C.

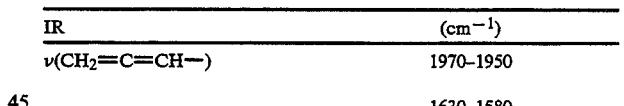

| IR | (cm⁻¹) |
|---|---|
| $\nu$(CH$_2$=C=CH—) | 1970–1950 |
| $\nu$(phenyl) | 1630–1580 |
| $\nu$(phenyl) | 1525–1460 |
| $\nu$(phenyl—O—CH=) | 1260–1200 |
| $\nu$(phenyl—Cl) | 1080–1040 |

| ¹H-NMR | (test solvent: CDCl$_3$) (standard: tetramethyl silan) $\delta$(ppm) |
|---|---|
| C$\underline{H}_2$=C=C— (2H, d) | 5.42–5.52 |
| =C=C$\underline{H}$—O— (1H, t) | 6.80–6.99 |

| IR | (cm$^{-1}$) |
|---|---|
| Ph—H (7H, m) | 7.00–7.60 |

[Example 7]
p-allenyloxyazobenzene
yield 22.3%
as a pale yellow oily product

| IR | (cm$^{-1}$) |
|---|---|
| ν(—N=N—) | 2045–2025 |
| ν(CH$_2$=C=CH—) | 1970–1950 |
| ν(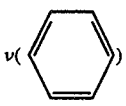) | 1630–1580 |
| ν(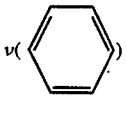) | 1525–1460 |
| ν(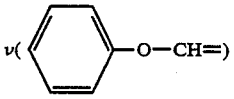) | 1260–1200 |

| $^1$H-NMR | (test solvent: CDCl$_3$) |
| | (standard: tetramethyl silan) |
| | δ(ppm) |
|---|---|
| CH$_2$=C=C— (2H, d) | 5.42–5.52 |
| =C=CH—O— (1H, t) | 6.80–6.99 |
| Ph—H (9H, m) | 7.00–7.60 |

[Example 8]
1-allenyloxy-10-methylanthracene
yield 53.0%
as crystals M.P. 78.2°–82.5° C.

| IR | (cm$^{-1}$) |
|---|---|
| ν(CH$_2$=C=CH—) | 1970–1950 |
| ν(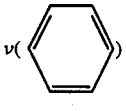) | 1630–1595 |
| ν(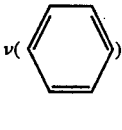) | 1525–1460 |
| ν(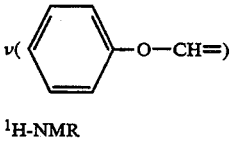) | 1260–1200 |

| $^1$H-NMR | (test solvent: CDCl$_3$) |
| | (standard: tetramethyl silan) |
| | δ(ppm) |
|---|---|
| CH$_2$=C=C— (2H, d) | 5.42–5.52 |
| =C=CH—O— (1H, t) | 6.80–6.99 |
| Ph—H (8H, m) | 7.00–7.50 |

[Example 9]
2,2'-diallenyloxybiphenyl
yield 63.2%
as an oily product

| IR | (cm$^{-1}$) |
|---|---|
| ν(CH$_2$=C=CH—) | 1970–1950 |
| ν(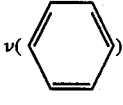) | 1630–1590 |
| ν(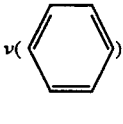) | 1525–1460 |
| ν(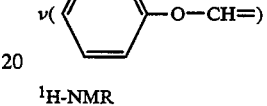) | 1260–1200 |

| $^1$H-NMR | (test solvent: CDCl$_3$) |
| | (standard: tetramethyl silan) |
| | δ(ppm) |
|---|---|
| CH$_2$=C=C— (4H, d) | 5.42–5.55 |
| =C=CH—O— (2H, t) | 6.80–6.99 |
| Ph—H (8H, m) | 7.10–7.61 |

EXAMPLE 10

Into a reaction flask fitted with a stirrer, a thermometer, a nitrogen gas inlet tube and a reflux condenser, were placed 19.276 parts of p-hydroxybenzoic acid, 50.242 parts of deionized water, 12.633 parts of NaOH and 0.011 part of tetrabutylammoniumbromide and to this mixture, 17.848 parts of propargyl bromide was added dropwise and reacted at 80° C. for 6 hours. After completion of the reaction, the content was treated with 1N-HCl and then with a mixture of ether and deionized water and the ether layer was separated, added with magnesium sulfate and kept standing overnight. After filtering off magnesium sulfate, the ether solvent was removed by an evaporator and the residue was subjected to a column chromatography (silica gel 200 mesh) to obtain a purified 1propargyloxybenzene-4-carboxylic acid. Yield 43.6%

Into a similar reaction vessel, as used in the above-mentioned reaction, were placed 7.920 parts of t-BuOK and 44.882 parts of t-BuOH and to this, a mixture of 10,000 parts of 1-propargyloxybenzene-4-carboxylic acid and 23.333 parts of t-BuOH was added dropwise. The content was reacted at 50° C. for 60 minutes and then a deionized water was added to stop the reaction. t-BuOH layer and water layer were removed by using an evaporator, and the residue was added with 1N-HCl and then extracted with an ether. The ether solvent was removed and the residue was subjected to a column chromatography (silica gel 200 mesh) to obtain a purified 1-allenyloxy benzene-4-carboxylic acid as a colorless clear oily product. This compound was identified by FT-NMR(H) and IR spectrum. The reaction yield was 43.0%.

| CH$_2$=C=CH—O—C$_6$H$_4$—COOH | |
|---|---|
| IR | (cm$^{-1}$) |
| ν(CH$_2$=C=CH—) | 1980–1950 |

-continued

CH₂=C=CH—O—C₆H₄—COOH

| IR | (cm⁻¹) |
|---|---|
| ν(⌬) | 1640–1560 |
| ν(⌬) | 1540–1480 |
| ν(—COOH) | 1780–1680 |
| ν(⌬—O—CH=) | 1280–1200 |

| ¹H-NMR | (test solvent: CDCl₃) (standard: tetramethyl silan) δ(ppm) |
|---|---|
| CH₂=C=C— (2H, d) | 5.47–5.50 |
| =C=CH—O— (1H, t) | 6.80–6.98 |
| Ph—H (4H, m) | 6.95–8.20 |

EXAMPLES 11 TO 18

The same experiments as stated in Example 10 were repeated using various hydroxy compounds and the following allene compounds were obtained.

[Example 11]
1-allenyloxybenzene-4-sulfonic acid
yield 56.5%
as a colorless clear oily product

| IR | (cm⁻¹) |
|---|---|
| ν(—SO₃H) | 3200–3000 |
| ν(CH₂=CH=CH—) | 1980–1940 |
| ν(⌬) | 1625–1595 |
| ν(⌬) | 1530–1480 |
| ν(—SO₃H) | 1260–1150 |

| ¹H-NMR | (test solvent: CDCl₃) (standard: tetramethyl silan) δ(ppm) |
|---|---|
| CH₂=C=C— (2H, d) | 5.42–5.80 |
| =C=CH—O— (1H, t) | 6.80–6.85 |
| Ph—H (4H, m) | 6.95–8.00 |

[Example 12]
2-allenyloxybiphenyl-5-carboxylic acid
yield 43.0%
as pale yellow crystals M.P. 122.5°–128.3° C.

| IR | (cm⁻¹) |
|---|---|
| ν(CH₂=C=CH—) | 1980–1940 |

-continued

| IR | (cm⁻¹) |
|---|---|
| ν(⌬) | 1620–1580 |
| ν(⌬) | 1520–1480 |
| ν(—COOH) | 1760–1680 |
| ν(⌬—O—CH=) | 1260–1200 |

| ¹H-NMR | (test solvent: CDCl₃) (standard: tetramethyl silan) δ(ppm) |
|---|---|
| CH=C=C— (2H, d) | 5.42–5.60 |
| =C=CH—O— (1H, t) | 6.80–6.89 |
| Ph—H (8H, m) | 6.95–8.15 |

[Example 13]
2-allenyloxynaphthalene-6-sulfonic acid
yield 45.3%
as white crystals M.P. 80.5°–83.5° C.

| IR | (cm⁻¹) |
|---|---|
| ν(CH₂=C=CH—) | 1980–1940 |
| ν(⌬) | 1625–1595 |
| ν(⌬) | 1525–1495 |
| ν(—SO₃H) | 1260–1150 |

| ¹H-NMR | (test solvent: CDCl₃) (standard: tetramethyl silan) δ(ppm) |
|---|---|
| CH₂=C=C— (2H, d) | 5.42–5.45 |
| =C=CH—O— (1H, t) | 6.89–6.98 |
| pH—H (6H, m) | 7.10–7.12 |

[Example 14]
4,4-bis(p-allenyloxyphenyl)valeric acid
yield 45.3%
as a colorless clear oily product

| IR | (cm⁻¹) |
|---|---|
| ν(CH₂=C=CH—) | 1970–1940 |
| ν(⌬) | 1640–1560 |
| ν(⌬) | 1530–1480 |

| IR | (cm⁻¹) |
|---|---|
| ν(⬡—COOH) | 1780–1680 |
| ν(⬡—O—CH=) | 1280–1200 |

¹H-NMR (test solvent: CDCl₃D)
(standard: tetramethyl silan)
δ(ppm)

| | |
|---|---|
| C$\underline{H}_2$=C=C— | 5.42–5.44 |
| =C=C$\underline{H}$—O— | 6.80–6.81 |
| Ph—$\underline{H}$ | 6.90–7.23 |

[Example 15]
2,2'-diallenyloxybiphenyl-3-carboxylic acid
yield 44.0%
as pale yellow crystals M.P. 40.5°–43.3° C.

| IR | (cm⁻¹) |
|---|---|
| ν(CH₂=C=CH—) | 1970–1940 |
| ν(⬡) | 1640–1560 |
| ν(⬡) | 1530–1480 |
| ν(—COOH) | 1780–1680 |
| ν(⬡—O—CH=) | 1280–1200 |

¹H-NMR (test solvent: CDCl₃)
(standard: tetramethyl silan)
δ(ppm)

| | |
|---|---|
| C$\underline{H}_2$=C=C— (4H, d) | 5.42–5.50 |
| =C=C$\underline{H}$—O— (2H, t) | 6.80–6.89 |
| Ph—$\underline{H}$ (7H, m) | 6.95–8.10 |

[Example 16]
1,4-diallenyloxynaphthalene-2-carboxylic acid
yield 52.3%
as pale yellow crystals M.P. 77.3°–82.3° C.

| IR | (cm⁻¹) |
|---|---|
| ν(CH₂=C=CH—) | 1970–1940 |
| ν(⬡) | 1640–1560 |
| ν(⬡) | 1530–1480 |
| ν(—COOH) | 1780–1680 |
| ν(⬡—O—CH=) | 1280–1200 |

¹H-NMR (test solvent: CDCl₃)
(standard: tetramethyl silan)
δ(ppm)

| | |
|---|---|
| C$\underline{H}_2$=C=C— (4H, d) | 5.42–5.45 |
| =C=C$\underline{H}$—O— (2H, t) | 6.89–6.98 |
| Ph—$\underline{H}$ (5H, m) | 7.10–8.10 |

[Example 17]
3-allenyloxyanthracene-2-carboxylic acid
yield 32.0%
as crystals M.P.178.2°–182.5° C.

| IR | (cm⁻¹) |
|---|---|
| ν(CH₂=C=CH—) | 1970–1940 |
| ν(⬡) | 1640–1580 |
| ν(⬡) | 1530–1480 |
| ν(—COOH) | 1780–1680 |
| ν(⬡—O—CH=) | 1280–1200 |

¹H-NMR (test solvent: CDCl₃)
(standard: tetramethyl silan)
δ(ppm)

| | |
|---|---|
| C$\underline{H}_2$=C=C— | 5.44–5.50 |
| =C=C$\underline{H}$—O— | 6.89–6.98 |
| Ph—$\underline{H}$ | 7.10–8.10 |

[Example 18]
1-allenyloxy-2-methylbenzene-4-sulfonic acid
yield 43.2%
as an oily product

| IR | (cm⁻¹) |
|---|---|
| ν(CH₂=C=CH—) | 1980–1940 |
| ν(⬡) | 1625–1595 |
| ν(⬡) | 1525–1495 |
| ν(—SO₃H) | 1260–1150 |

¹H-NMR (test solvent: CDCl₃)
(standard: tetramethyl silan)

-continued

| IR | (cm$^{-1}$) |
|---|---|
| | δ(ppm) |
| C$\underline{H}_2$=C=C— (2H, d) | 5.44–5.50 |
| =C=C$\underline{H}$—O— (1H, t) | 6.89–6.98 |
| Ph—$\underline{H}$ (3H, m) | 7.20–8.10 |

EXAMPLE 19

Into a reaction flask fitted with a stirrer, a thermometer, a nitrogen gas inlet tube and a reflux condenser, were placed 19.06 parts of 2,2′-bis(4-hydroxyphenyl)-propane, 2.39 parts of deionized water, 7.18 parts of NaOH, 0.162 part of tetrabutylammonium bromide and 78.65 parts of dioxane and to this mixture, 21.36 parts of propargyl bromide was added dropwise and reacted at 80° C. for 4 hours. After completion of the reaction, dioxane was distilled off and the residue was treated with a mixture of ether and deionized water and with 1N-NaOH aqueous solution. The ether layer was separated, added with magnesium sulfate and kept standing overnight to effect dehydration. After filtering off magnesium sulfate, the ether solvent was removed by an evaporator to obtain crystalline form of 2,2′bis (4-propargyloxyphenyl)propane. M.P. 76.5° C., Yield 63.6%

Into a similar reaction vessel, as used in the above-mentioned reaction, were placed 0.92 parts of t-BuOK and 4.76 parts of t-BuOH and to this, after completely dissolved, a solution of 5.00 parts of 2,2′-bis(4-propargyloxyphenyl)propane in 10.99 parts of t-BuOH was dropwise added. The content was reacted at 60° C. for 30 minutes and then a deionized water was added to stop the reaction. The t-BuOH layer and the water layer was separated. The water layer was then extracted with ether. The BuOH layer and ether extract were combined and the solvents were removed by using an evaporator to obtain a brown colored liquid. Said liquid was purified by subjecting to a column chromatography (silica gel 200 mesh) to obtain a purified 2,2′-bis(4-allenyloxyphenyl)propane as a colorless clear oily product. This compound was identified by FT-NMR(H) and IR spectrum. The reaction yield was 43.0%.

| IR | (cm$^{-1}$) |
|---|---|
| ν(—CH$_3$) | 2990–2975 |
| ν(CH$_2$=C=CH—) | 1980–1940 |
| ν(⌬) | 1625–1595 |
| ν(⌬) | 1540–1495 |
| ν(—CH$_3$) | 1460–1420 |
| ν(⌬—O—CH=) | 1260–1200 |

| $^1$H-NMR | (test solvent: CDCl$_3$) |
|---|---|
| | (standard: tetramethyl silan) |
| | δ(ppm) |
| C$\underline{H}_2$=C=C— | 5.42–5.55 |
| =C=C$\underline{H}$—O— | 6.72–6.88 |
| Ph—$\underline{H}$ | 6.90–7.30 |
| C$\underline{H}_3$ | 1.60–1.85 |

EXAMPLES 20–25

Similar experiments as stated in Example 19 were repeated using the following phenol compounds:
- bis(4-hydroxyphenyl) methane
- 1,1′-bis(4-hydroxyphenyl) cyclohexane
- 1,1-bis(2-methyl-4-hydroxy-5-butylphenyl) butane
- bis(4-hydroxy-2-chlorophenyl) methane

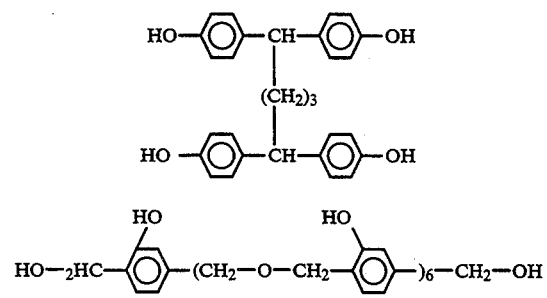

The following allene compounds were obtained.

[Example 20]
Bis (4-allenyloxyphenyl) methane
yield 53.0%
as a colorless clear oily product

| IR | (cm$^{-1}$) |
|---|---|
| ν(—CH$_2$—) | 2930–2920 |
| ν(CH$_2$=C=CH—) | 1980–1940 |
| ν(⌬) | 1620–1595 |
| ν(⌬) | 1540–1495 |
| ν(—CH$_2$—) | 1460–1420 |
| ν(⌬—O—CH$_2$—) | 1250–1200 |

| $^1$H-NMR | (test solvent: CDCl$_3$) |
|---|---|
| | (standard: tetramethyl silan) |
| | δ(ppm) |
| CH$_2$=C=C— | 5.41–5.45 |
| =C=CH—O— | 6.80–6.95 |
| Ph—$\underline{H}$ | 6.96–7.30 |
| —C$\underline{H}_2$— | 2.54–2.60 |

[Example 21]
1,1′-bis(4-allenyloxyphenyl) cyclohexane
yield 43.5%
as a colorless clear oily product

| IR | (cm⁻¹) |
|---|---|
| $\nu$(—CH$_2$—) | 2930–2920 |
| $\nu$(CH$_2$=C=CH—) | 1980–1940 |
| $\nu$(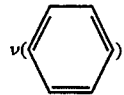) | 1625–1595 |
| $\nu$(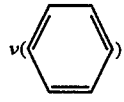) | 1525–1495 |
| $\nu$(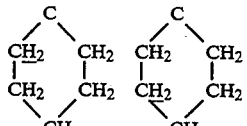—O—CH=) | 1260–1200 |
| (cyclo ring) | 1480–1440 |

¹H-NMR (test solvent: CDCl$_3$) (standard: tetramethyl silan) $\delta$(ppm)

| | |
|---|---|
| CH$_2$=C=C— | 5.41–5.44 |
| =C=C$\underline{H}$—O— | 6.80–6.88 |
| Ph—$\underline{H}$ | 6.96–7.45 |
| 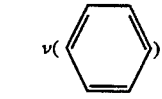 | 0.82–1.82 |

[Example 22]
1,1-bis (2-methyl-4-allenyloxy-5-butylphenyl)butane
yield 55.0%
as a colorless clear oily product

| IR | (cm⁻¹) |
|---|---|
| $\nu$(—CH$_3$, —CH$_2$—) | 2980–2920 |
| $\nu$(CH$_2$=C=CH—) | 1980–1940 |
| $\nu$(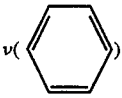) | 1630–1590 |
| $\nu$(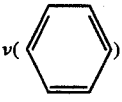) | 1520–1490 |
| (—CH$_2$CH$_2$CH$_3$) | 740–720 |

¹H-NMR (test solvent: CDCl$_3$) (standard: tetramethyl silan) $\delta$(ppm)

| | |
|---|---|
| CH$_2$=C=C— | 5.41–5.44 |
| =C=C$\underline{H}$—O— | 6.85–6.95 |
| Ph—$\underline{H}$ | 6.98–7.35 |

[Example 23]
bis(4-allenyloxy-2-chlorophenyl)methane
yield 45.0%
as an oily product

| IR | (cm⁻¹) |
|---|---|
| $\nu$(—CH$_2$—) | 2930–2920 |
| $\nu$(CH$_2$=C=CH—) | 1970–1950 |
| $\nu$(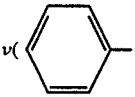) | 1620–1595 |
| $\nu$(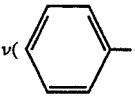) | 1540–1495 |
| $\nu$(—CH$_2$—) | 1460–1420 |
| | 1250–1200 |
| $\nu$(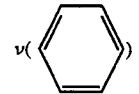—O—CH=) | |
| $\nu$(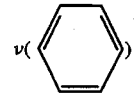—Cl) | 1100–1050 |

¹H-NMR (test solvent: CDCl$_3$) (standard: tetramethyl silan) $\delta$(ppm)

| | |
|---|---|
| CH$_2$=C=C— | 5.42–5.46 |
| =C=C$\underline{H}$—O— | 6.85–6.90 |
| Ph—$\underline{H}$ | 6.98–7.35 |
| —C$\underline{H_2}$— | 2.54–2.55 |

[Example 24]

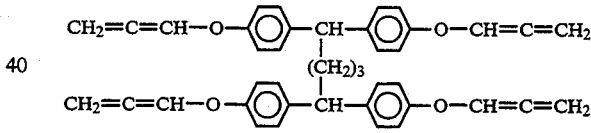

yield 23.3%
as an oily product

| IR | (cm⁻¹) |
|---|---|
| $\nu$(—CH$_2$—) | 2930–2920 |
| $\nu$(CH$_2$=C=CH—) | 1980–1940 |
| $\nu$(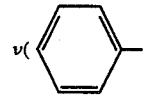) | 1620–1595 |
| $\nu$( ) | 1540–1495 |
| $\nu$(—CH$_2$—) | 1460–1420 |
| $\nu$( —O—CH=) | 1250–1200 |

¹H-NMR (test solvent: d-DMSO) (standard: tetramethyl silan)

| IR | (cm$^{-1}$) |
|---|---|
| | δ(ppm) |
| CH$_2$=C=C— | 5.41–5.45 |
| =C=CH—O— | 6.83–6.93 |
| Ph—H | 6.98–7.45 |

[Example 25]

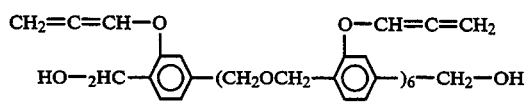

yield 15.2%
as a pale yellow solid

| IR | (cm$^{-1}$) |
|---|---|
| ν(—CH$_2$OH) | 3300–3200 |
| ν(—CH$_2$—) | 2930–2920 |
| ν(CH$_2$=C=CH—) | 1980–1940 |
| ν(⟨benzene⟩) | 1620–1595 |
| ν(⟨benzene⟩) | 1540–1495 |
| ν(—CH$_2$—) | 1460–1420 |
| ν(⟨benzene⟩—O—CH=) | 1250–1200 |
| ν(—CH$_2$OCH$_2$—) | 1120–1080 |
| $^1$H-NMR | (test solvent: d-DMSO) |
| | (standard: tetramethyl silan) |
| | δ(ppm) |
| CH$_2$=C=C— | 5.41–5.40 |
| =C=CH—O— | 6.85–6.95 |
| Ph—H | 6.98–7.85 |

EXAMPLE 26

Into a reaction flask fitted with a stirrer, a thermometer, a nitrogen gas inlet tube and a reflux condenser, were placed 13.469 parts of 1,4-dihydroxybenzene, 44.037 parts of deionized water, 11.070 parts of NaOH and 0.134 part of tetrabutylammonium bromide and dissolved. To this, 31.288 parts of propargyl bromide were dropwise added in 15 minutes and the content was reacted at 80° C. for 6 hours.

After completion of the reaction, the content was treated with ether/deionized water and with 1N-NaOH aqueous solution and the ether layer was separated. To this ether solution, magnesium sulfate was added and the combined was kept standing overnight to effect dehydration. After removing magnesium sulfate, the solvent was evaporated to obtain an oily product. This was purified by using a column chromatography (silica gel mesh 200) with a developer of ethyl acetate/hexane to obtain a purified 1,4-dipropargyloxybenzene. Yield 79.6%

Into a similar reaction vessel, as used in the above-mentioned reaction, were placed 2.984 parts of t-BuOK and 16.906 parts of t-BuOH, and to this, was added dropwise a solution of 10.00 parts of 1,4-dipropargyloxybenzene in 23.333 parts of t-BuOH in 15 minutes. The combined was reacted at 60° C. for 30 minutes and thereafter, added with deionized water to stop the reaction.

The t-BuOH layer and aqueous layer were separated from each other.

The aqueous layer was extracted with ether. Thus obtained ether extract and t-BuOH layer were combined together and the solvents were removed out by using an evaporator to obtain a brown colored oily product.

The crude oil was purified by means of column chromatography (silica gel mesh 200) with a developer of ethyl acetate/hexane and 1,4-diallenyloxy benzene was obtained as white crystals (M.P.34.2°–36.7° C.). This compound was identified by FT-NMR(H) and IR means. Yield: 62.3%

| IR | (cm$^{-1}$) |
|---|---|
| ν(CH$_2$=C=CH—) | 1980–1950 |
| ν(⟨benzene⟩) | 1625–1575 |
| ν(⟨benzene⟩) | 1525–1495 |
| ν(⟨benzene⟩—O—CH=) | 1260–1200 |
| ν(CH$_2$=C=) | 895–885 |
| $^1$H-NMR | (test solvent: CDCl$_3$) |
| | (standard: tetramethyl silan) |
| | δ(ppm) |
| CH$_2$=C=C— | 5.41–5.45 |
| =C=CH—O— | 6.72–6.88 |
| Ph—H | 6.90–7.30 |

EXAMPLE 27

The similar experiments were carried out as in Example 26, excepting substituting 1,3,5-trihydroxybenzene for 1,4-dihydroxybenzene.

1,3,5-triallenyloxy benzene was obtained as a colorless oily product. Yield 52.3%

| IR | (cm$^{-1}$) |
|---|---|
| ν(CH$_2$=C=CH—) | 1975–1950 |
| ν(⟨benzene⟩) | 1625–1575 |
| ν(⟨benzene⟩) | 1525–1475 |

-continued

| IR | (cm⁻¹) |
|---|---|
| ν(⟨phenyl⟩—O—CH=) | 1250–1200 |
| ν(CH₂=C=) | 895–885 |
| ¹H-NMR | (test solvent: CDCl₃) (standard: tetramethyl silan) δ(ppm) |
| C$\underline{H}_2$=C=C— | 5.41–5.45 |
| =C=C$\underline{H}$—O— | 6.80–6.92 |
| Ph—$\underline{H}$ | 6.95–7.50 |

EXAMPLE 28

Into a reaction flask fitted with a stirrer, a thermometer, a nitrogen gas inlet tube and a reflux condenser, were placed 10.879 parts of phenol, 20.808 parts of deionized water and 5.345 parts of NaOH and to this mixture, 14.784 parts of propargyl bromide was added dropwise in 15 minutes and the combined was reacted at 40° C. for 15 hours. Next, AlCl₃ and 14.784 parts of propargyl bromide were added and the reaction was continued for an additional 10 hours. Thereafter, the content was treated and purified as in Example 27 to obtain 1-propargyloxy-4-propargylbenzene as an oily product. Yield 26.7%

(—CH₂—C≡CH) 1420 cm⁻¹

Into a similar reaction vessel as used in the abovementioned reaction, were placed 1.492 parts of t-BuOK and 8.453 parts of t-BuOH, and to this, was added dropwise a solution of 5.00 parts of 1-propargyloxy-4-propargylbenzene in 11.667 parts of t-BuOH in 15 minutes. The combined was reacted at 50° C. for 60 minutes and thereafter, added with deionized water to stop the reaction.

The t-BuOH layer and aqueous layer were separated from each other.

The aqueous layer was extracted with ether. Thus obtained ether extract and t-BuOH layer were combined together and the solvents were removed by using an evaporator to obtain a brown colored oily product.

The crude oil was purified by means of column chromatography (silica gel mesh 200) with a developer of ethyl acetate/hexane and 1-allenyloxy-4-allenyl benzene was obtained as a colorless oil. This compound was identified by FT-NMR(H) and IR means.
Yield: 52.3%

| IR | (cm⁻¹) |
|---|---|
| ν(CH₂=C=CH—) | 1970–1950 |
| ν(⟨phenyl⟩) | 1620–1595 |
| ν(⟨phenyl⟩) | 1520–1480 |

-continued

| IR | (cm⁻¹) |
|---|---|
| ν(⟨phenyl⟩—O—CH=) | 1260–1200 |
| ν(CH₂=C=) | 895–885 |
| ¹H-NMR | (test solvent: CDCl₃) (standard: tetramethyl silan) δ(ppm) |
| C$\underline{H}_2$=C=C— | 5.44–5.46 |
| =C=C$\underline{H}$—O— | 6.80–6.90 |
| Ph—$\underline{H}$ | 6.90–7.30 |

EXAMPLES 29–30

The same experiments as stated in Example 26 were repeated using 1,4-dihydroxy-2,5-t-butyl benzene and 1,2,4,5-tetrahydroxybenzene as phenol compound, respectively. The following allene compounds were obtained.

[Example 29]
1,4-diallenyloxy-2,5-t-butylbenzene
yield 73.2%
as an oily product

| IR | (cm⁻¹) |
|---|---|
| ν(—CH₃) | 2980–2960 |
| ν(CH₂=C=CH—) | 1970–1950 |
| ν(⟨phenyl⟩) | 1625–1595 |
| ν(⟨phenyl⟩) | 1520–1495 |
| ν(—C(CH₃)₃) | 1280–1200 |
| ν(CH₂=C=) | 895–885 |
| ¹H-NMR | (test solvent: CDCl₃) (standard: tetramethyl silan) δ(ppm) |
| C$\underline{H}_2$=C=C— | 5.41–5.45 |
| =C=C$\underline{H}$—O— | 6.80–6.87 |
| Ph—$\underline{H}$ | 6.96–7.50 |
| C$\underline{H}_3$ | 1.15–1.30 |

[Example 30]
1,2,4,5-tetra-allenyloxybenzene
yield 65.3%
as an oily product

| IR | (cm⁻¹) |
|---|---|
| ν(CH₂=C=CH—) | 1970–1950 |
| ν(⟨phenyl⟩) | 1620–1580 |
| ν(⟨phenyl⟩) | 1520–1480 |

-continued

| IR | (cm$^{-1}$) |
|---|---|
| $\nu($ ⌬ $-$O$-$CH$=$) | 1280–1200 |
| $\nu($CH$_2$=C=) | 895–885 |
| $^1$H-NMR | (test solvent: CDCl$_3$) |
| | (standard: tetramethyl silan) |
| | δ(ppm) |
| C$\underline{H}_2$=C=C— | 5.41–5.46 |
| =C=C$\underline{H}$—O— | 6.82–6.88 |
| Ph—$\underline{H}$ | 6.98–7.32 |

EXAMPLE 31

Preparation of propargyl phenyl ether

Into a 500 ml 3-necked flask fitted with a stirrer, a thermometer, condenser and a decanter, were placed 100 parts of benzene, 23.2 parts (0.2 mol) of sodium phenolate and 57.8 parts (0.22 mol) of triphenylphosphine and the mixture was refluxed for 30 minutes to remove water contained in the system.

Then, 56.06 parts (1.0 mol) of propargyl alcohol and 30 parts of carbontetrachloride were added and the combined was heated and refluxed for 3 hours. After cooling, the formed sodium chloride was filtered off and the filtrate was concentrated by using an evaporator and then added with hexane. The formed precipitates were filtered off and the filtrate was washed with an aqueous NaOH solution and dried with magnesium sulfate.

The hexane solution was then concentrated to obtain 11.8 parts (yield 44.7%) of crude propargylphenylether. This compound was identified by $^1$H-NMR means:

$^1$H-NMR(ppm)
  2.49(1HS, C$\underline{H}$)
  4.65 (2HS, C$\underline{H}_2$—O)
  6.89–7.34 (5H, ph-$\underline{H}$)

EXAMPLE 32

Preparation of allenylphenyl ether

Into a 50 ml 3-necked flask fitted with a stirrer, a thermometer, and a condenser, were placed 1.06 parts of t-BuOK and 5.49 parts of t-BuOH and dissolved. To this, a mixture of 5.0 parts of propargylphenylether and 11 parts of t-BuOH was dropwise added in 1 hour and the combined mixture was heated to 60° C. and maintained at the same temperature for 15 minutes and then cooled.

20 parts of pure water were added to the reaction mixture to stop the reaction and the mixture was extracted with ether.

The extract was concentrated to obtain 3.58 parts (yield 71.6%) of allenylphenylether. This compound was identified by means of $^1$H-NMR.

| $^1$H-NMR(ppm) | |
|---|---|
| C$\underline{H}_2$=C=C | 5.38–5.40 (1H, t) |
| =C=C$\underline{H}$—O— | 6.78–6.80 (2H, d) |
| Ph—$\underline{H}$ | 7.0–7.28 (5H, m) |

EXAMPLE 33

Preparation of 4,4′-dipropargyloxy bi phenyl

Into a 500 ml 3-necked flask fitted with a stirrer, a thermometer, condenser and a decanter, were placed 100 parts of benzene, 18.6 parts (0.1 mol) of sodium phenolate and 57.8 parts (0.22 mol) of triphenylphosphine and the mixture was refluxed for 30 minutes to remove water contained in the system.

Then, 56.06 parts (1.0 mol) of propargyl alcohol and 30 parts of carbontetrachloride were added and the combined was heated and refluxed for 3 hours. After cooling, the formed sodium chloride was filtered off and the filtrate was concentrated by using an evaporator and then added with hexane.

The formed precipitates were filtered off and the filtrate was washed with an aqueous NaOH solution and dried with magnesium sulfate.

The hexane solution was then concentrated to obtain 11.0 parts (yield 42.0%) of crude 4,4′-dipropargyloxy biphenyl. This compound was identified by $^1$H-NMR means:

$^1$H-NMR(ppm)
  2.54 (2H, s, CH≡)
  4.72 (4H, s, —CH$_2$—O)
  6.90–7.60 (8H, m ph-H)

EXAMPLE 34

Preparation of 4,4′-diallenyloxy biphenyl

Into a 50 ml 3-necked flask fitted with a stirrer, a thermometer, and a condenser, were placed 1.06 parts of t-BuOK and 5.50 parts of t-BuOH and dissolved. To this, a mixture of 5.42 parts (0.02 mol) of 4,4′-dipropargyloxybiphenyl and 11 parts of t-BuOH was added dropwise in 1 hour and the combined mixture was heated to 60° C. and maintained at the same temperature for 15 minutes and then cooled.

20 parts of pure water were added to the reaction mixture to stop the reaction and the mixture was extracted with ether. The extract was concentrated to obtain 3.4 parts (yield 65%) of 4,4′-diallenyloxybiphenyl. This compound was identified by means of $^1$H-NMR.

| $^1$H-NMR(ppm) | |
|---|---|
| C$\underline{H}_2$=C=C— | 5.46–5.50 (4H, d) |
| =C=C$\underline{H}$—O— | 6.86–6.89 (2H, t) |
| Ph—$\underline{H}$ | 7.00–7.60 (8H, m) |

What is claimed is:

1. An allene compound of the formula:

$$(CH_2=C=CH-O)_n-R-(A)_m \qquad (I)$$

in which R is an aromatic group selected from the group consisting of benzene, naphthalene, anthracene, azobenzene, bisphenol, or polyphenyl having 2 to 10 benzene rings directly and linearly connected with each other, or $$-ph-R^1-ph- \text{ group} \qquad (II)$$

in which each ph represents a phenylene, and R$^1$ is a bivalent C$_1$–C$_6$ aliphatic hydrocarbon, an alicyclic hydrocarbon or C$_2$–C$_6$ aliphatic hydrocarbon whose main chain is interrupted by one or more oxygen atoms or R is any of the above-mentioned aromatic groups substituted by one or more of groups selected from halogen, alkyl, cyano or alkoxy; A is a carboxyl, sulpho or —CH═C═CH$_2$ group; n is an integer of from 1 to 10; m is 0, 1, 2, or 3, the sum of said m and n being equal to the valence of R, excluding the case wherein R is a halogen, methyl, cyano- or methoxy- substituted or unsubstituted benzene, n is 1 and m is 0, and excluding the case wherein R is an unsubstituted napthalene, n is 1 and m is 0.

2. The compound according to claim 1, wherein R is an aromatic group selected from the group consisting of benzene, naphthalene, anthracene, azobenzene or polyphenyl having 2 to 10 benzene rings directly and linearly connected with each other, or any of the above-mentioned aromatic groups substituted by one or more of halogen, alkyl, cyano or alkoxy groups; A is carboxyl or sulpho group; n is an integer from 1 to 10 and m is 1, 2 or 3.

3. The compound according to claim 1, wherein R is an aromatic group selected from naphthalene, anthracene, azobenzene or polyphenyl having 2 to 10 benzene rings directly and linearly connected with each other, or any of the above-mentioned aromatic groups substituted by one or more of halogen, alkyl, cyano or alkoxy groups; n is 1, 2 or 3 and m is 0, except in the case wherever R is an unsubstituted naphthalene, n is 1 and m is 0.

4. The compound according to claim 1, wherein R is a —ph—R$^1$—ph group in which ph stands for a phenylene group or a phenylene substituted by one or more of halogen, alkyl, cyano or alkoxy groups, and R$^1$ is a bivalent C$_1$–C$_6$ aliphatic hydrocarbon, an alicyclic hydrocarbon or a C$_2$–C$_6$ aliphatic hydrocarbon interrupted by one or more oxygen atoms, n is 2 and m is 0.

5. The compound according to claim 1, wherein R is a benzene, or benzene substituted with up to 4 substituents selected from halogen atoms, alkyl groups, cyano groups or alkoxy groups, A is a —CH═C═CH$_2$ group, m is 0, 1 or 2, and n is an integer of from 1 to 4, provided that the sum of m and n is 2 or more.

6. A process for the preparation of an allene compound of the formula:

$$(CH_2=C=CH-O)_n-R-(A)_m \qquad (I)$$

in which R is a benzene or benzene substituted with up to 4 substituents selected from halogen atoms, alkyl groups, cyano groups or alkoxy groups, A is a —CH═C═CH$_2$ group, m is 1 or 2 and n is an integer of from 1 to 4, which comprises reacting a compound of the formula:

$$(CH\equiv C-CH_2-O-)_n-R \qquad (IV)$$

in which n and R each have the same meanings as defined above, in respect to formula (I), with a propargyl halide in a molar ratio of m moles of propargyl halide per mole of compound of the formula (IV), to give a compound of the formula:

$$(CH\equiv C-CH_2-O)_n-R-(CH_2-C\equiv CH)_m$$

and then subjecting the compound to an isomerization at a reaction temperature in the presence of a basic compound to produce the desired allene compound.

* * * * *